(12) United States Patent
Foung et al.

(10) Patent No.: US 7,879,326 B2
(45) Date of Patent: Feb. 1, 2011

(54) HUMAN NEUTRALIZING MONOCLONAL ANTIBODIES TO H5N1 INFLUENZA A VIRUS

(75) Inventors: Steven Foung, Stanford, CA (US); Zhen-Yong Keck, Redwood City, CA (US); Richard Webby, Memphis, TN (US)

(73) Assignees: The Board of Trustees of the Leland Stanford Junior University, Palo Alto, CA (US); St. Jude Children's Research Hospital, Memphis, TN (US)

( * ) Notice: Subject to any disclaimer, the term of this patent is extended or adjusted under 35 U.S.C. 154(b) by 164 days.

(21) Appl. No.: 12/140,151

(22) Filed: Jun. 16, 2008

(65) Prior Publication Data

US 2009/0041679 A1 Feb. 12, 2009

Related U.S. Application Data

(60) Provisional application No. 60/944,381, filed on Jun. 15, 2007.

(51) Int. Cl.
*A61K 39/42* (2006.01)
*C07K 16/10* (2006.01)
*C12N 15/13* (2006.01)
*C12N 5/24* (2006.01)
*C12N 5/10* (2006.01)

(52) U.S. Cl. ............ 424/142.1; 424/147.1; 530/388.15; 530/388.3; 536/23.52; 435/339

(58) Field of Classification Search ........................ None
See application file for complete search history.

(56) References Cited

U.S. PATENT DOCUMENTS 6,069,301 A * 5/2000 Carozzi et al. .............. 800/302
7,396,915 B2 * 7/2008 Hosokawa et al. ....... 530/387.7
2005/0170334 A1 8/2005 Mikayama et al.

FOREIGN PATENT DOCUMENTS

WO 03/048328 6/2003
WO WO 03/048328 * 6/2003

OTHER PUBLICATIONS

Paul, Fundamental Immunology, (textbook), 1993, pp. 292-295.*
"Continuing progress towards a unified nomenclature system for the highly pathogenic H5N1 avian influenza viruses" [online, retrieved Apr. 6, 2010] <URL http://www.who.int/csr/disease/avian_influenza/guidelines/nomenclature/en/index.html>.*
"Neighbor-joining (NJ) tree . . . " [online, retrieved Apr. 6, 2010] <URL http://who.int/csr/disease/avian_influenza/H5Trimmedtree.pdf>.*
Chen et al (Nature 436:191-192, 2005).*
Simmons et al (Plos Medicine 4: e178, May 2007).*
Chen; et al, "H5N1 virus outbreak in migratory waterfowl", Nature, Jul. 14, 2005, 436:191-192.
Simmons; et al., "Prophylactic and Therapeutic Efficacy of Human Monoclonal Antibodies against H5N1 Influenza", PLOS Medicine, May 2007, 4(5)(e178):0928-0936.
Treanor; et al., "Safety and Immunogenicity of an Inactivated Subvirion Influenza A (H5N1) Vaccine", New England Journal of Medicine, Mar. 30, 2006, 354(13):1343-1351.
Wu; et al., "Ultra-potent Antibodies Against Respiratory Syncytial Virus: Effects of Binding Kinetics and Binding Valence on Viral Neutralization", J. Mol. Biol., 2005, 350:126-144.

* cited by examiner

*Primary Examiner*—Mary E Mosher
(74) *Attorney, Agent, or Firm*—Bozicevic, Field & Francis LLP; Pamela J. Sherwood

(57) ABSTRACT

A panel of $IgG_1$ human monoclonal antibodies (HMAbs) identified by hemagglutination inhibition (HI) assay has been produced from peripheral B cells of an individual immunized with prototype H5N1 vaccine. Sequence analysis of antibody clones showed three clusters of different HMAbs as represented by HMAbs designated as BF1-1, BF1-19 and BF1-10. BF1-1 and BF1-10 have distinct CDR 1, 2 and 3 regions of both heavy and light chains. BF1-19 has the same heavy chain as BF1-1 but the light chain of BF1-10. Antibody binding affinity, $K_D$, studies showed all three HMAbs ranging from at least about $10^{-8}$ to at least about $10^{-9}$. In vivo protection studies showed that these antibodies afforded significant protection against infection. These findings demonstrate that the antibodies of the invention are cross-neutralizing and therapeutic.

11 Claims, 8 Drawing Sheets

Fig. 3A

BF1-1 Heavy Chain (SEQ ID NO:1)
GAGGTGCAGCTGGTGCAGTCTGGCCCAGGACTGGTGAAGCCTTCGGAGACCCTGTCCCTCACTTGCACTGTCTCTGGTAGCTCCATGAGGACT
CACTATTGGACCTGGATCCGGCAGCCCCCAGGGAAGGGACTGGAGTGGATTGGGAACATCTATTACAGTGGGAGCACCGACTACAACCCCTCC
CTCAAGAGTCGAGTCACCATATCAGTAGACACGTCCAAGAACCAGTTCTCCCTGAAACTGAGCTCTGTGACCGCCGCAGACACGGCCGTGTAT
TTTTGTGCGAGAACAAAACACTTCGATATTTTGCCCGGGGGTGTTTTTGATATGTGGGGCCGAGGGACCACGGTCACCGTCTCCTCA

Fig. 3B

BF1-1 Light Chain (SEQ ID NO:2)
TCTTCCTATGAGCTGACGCAGCTACCCTCAGTGTCCGTGTCCCCAGGACAGACAGCCACCATCACCTGCTCTGGAGATAGATTGGGGGATAAAA
TATGCTTGCTGGTATCAGCAGAAGCCAGGCCAGTCCCCTGTGCTGGTCATCTTTCAAGATACCAAGCGGCCCTCAGGGATCCCTGAGCGATTC
TCTGGCTCCAACTCTGGGAACACAGCCACTCTGACCATCAGCGGGACCCAGGCTATGGATGAGGCTGACTATTACTGTCAGGCGTGGGACAGC
AATATTGGGGTATTCGGCGGAGGGACCAAGCTCACCGTCCTA

Fig. 4A

BF1-10 Heavy Chain (SEQ ID NO:3)
CAGGTGCAGCTGCAGGAGTCGGGCCCAGGACTGGTGAAACCTTCACAGACCCTGTCCCTCACCTGCGCTGTCTCTGGTGGCTCCATCAGCAGT
CGTGGTTACTACTGGAGTTGGATCCGCCAGCCCCCAGGGAAGGGCCTGGAGTGGATTGGGTACATCTTTTACACGGGGACCACTACAAC
CCGTCCCTCAAGAGTCGAATTACCATATCAAGAGACACGCCCAAGAACCAGATATCCCTGAGCTCTGTGACTCTGAGACACGCC
GTGTATTACTGTGCCAGAGTGTGGATGGTGGTAGTAGTGGTATCATTACTACTTTGACTACTGGGGCCAGGGAACCCTGGTCACCGTCTCC
TCA

Fig. 4B

BF1-10 Light Chain (SEQ ID NO:4)
TCTGACATCCAGATGACCCAGTCTCCTGCTTCCGTTAGCTGTATCTCTGGGGCAGAGGGCCAGCATCTCATACAGGGCCAGCAAAAGTGTCAGT
ACATCTGGCTATAGTTATATGCACTGGAACCAGAAACAGAACAGCCCAGACTCCTCATCTATCTTGTATCCAACCTAGAATCTGGG
GTCCCTGCCAGGTTCAGTGGCAGTGGGTCTGGGACAGACTTCACCCTCAACATCCATCCTGTGGAGGAGGATGCTGCAACCTATTACTGT
CAGCACATTAGGGAGCTTACACGTTCGGAGGGGGGACCAAGCTGGAGATCAAACGT

Fig. 5A

BF1-19 Heavy Chain (SEQ ID NO:5)
CAGGTGCAGCTGCAGGAGTCGGGCCCAGGACTGGTGAAGCCTTCGGAGACCCTGTCCCTCACTTGCACTGTCTCTGGTAGCTTCCATGAGGACT
CACTATTGGACCTGGATCCGGCAGCCCCCAGGGAAGGGACTGGAGTGGATTGGGAACATCTATTACAGTGGAGCACCGACTACAACCCCTCC
CTCAAGAGTCGAGTCACCATATCAGTAGACACGTCCAAGAACCAGTTCTCCCTGAAACTGAGCTCTGTGACCGCCGCAGACACGGCCGTGTAT
TTTTGTGCGAGAACAAAACACTTCGATATTTTGCCCGGGTGTTTTGATATGTGGGGCCGAGGGACAATGGTCACCGTCTCTTCA

Fig. 5B

BF1-19 Light Chain (SEQ ID NO:6)
TCTGACATCGTGATGACCCAGTCTCCTGCTTCCTTAGCTGTATCTCTGGGGCAGAGAGGGCCACCATCTCATACAGGCCAGCAGCAAAGTGTCAGT
ACATCTGGCTATAGTTATATGCACTGGAACCAGAAACCAGGACAGCCCAGACTCCTCATCTATCCAACCTAGAATCTGGG
GTCCCTGCCAGGTTCAGTGGCAGTGGGTCTGGGACAGACTTCACCCTCAACATCATCCTGTGGAGGAGGATGCTGCAACCTATTACTGT
CAGCACATTAGGGAGCTTACACGTTCGGAGGGGGGACCAAAGTGGATATCAAACGT

Fig. 6A

BF1-1 Heavy Chain (SEQ ID NO:7)

EVQLVQSGPGLVKPSETLSLTCTVSGSS <u>MRTHY</u> WTWIRQPPGKGLEWIGNI <u>YYSGSTD</u>
                                                 *CDR1*                                *CDR2*

YNPSLKSRVTISVDTSKNQFSLKLSSVTAADTAVYFCAR <u>IKHFDILPGGVEDMWGRGT</u>
                                                         *CDR3*

TVTVSS

Fig. 6B

BF1-1 Light Chain (SEQ ID NO:8)

SYELTQLPSVSVSPGQTATITCSGD <u>RLGDKY</u> ACWYQQKPGQSPVLVIF <u>QDIKRPS</u> GIP
                                *CDR1*                                     *CDR2*

ERFSGSNSGNTATLLTISGTQAMDEADYYC <u>QAWDSNIGV</u> FGGGTKLTVL
                                        *CDR3*

Fig. 7A

BF1-10 Heavy Chain (SEQ ID NO:9)

QVQLQESGPGLVKPSQTLSLTCAVSGGSISSRGYYYWSWIRQPPGKGLEWIGYIFYIGG

TDYNPSLKSRITISRDTPKNQISLNLSSVTAADTAVYYCARVVDGSSGYHHYYFDYWG

QGTLVTVSS

CDR1: SRGYYYWS
CDR2: IFYIGGTDYNPSLKS
CDR3: VVDGSSGYHHYYFDY

Fig. 7B

BF1-10 Light Chain (SEQ ID NO:10)

DIQMTQSPASLAVSLGQRATISYRASKSVSTSGYSYMHWNQQKPGQPPRLLIYLVSN

LESGVPARFSGSGSGTDFTLNIHPVEEEDAATYYCQHIRELTRSEGGPSWRSN

CDR1: RASKSVSTSGYSYMH
CDR2: LVSNLES
CDR3: QHIRELTRSEGGPSWRSN

Fig. 8A

BF1-19 Heavy Chain (SEQ ID NO:11)

QVQLQESGPGLVKPSETLSLTCTVSG SSMRTHY WTWIRQPPGKGLEWIGN IYYSGST

DYNPSLKSRVTISVDTSKNQFSLKLSSVTAADTAVYFCAR TKHFDILPGGVFDMWGR

GTTVSS

CDR1: SSMRTHY
CDR2: IYYSGST
CDR3: TKHFDILPGGVFDMWGR

Fig. 8B

BF1-19 Light Chain (SEQ ID NO:12)

DIVMTQSPASLAVSLGQRATISYRASKSVSTSGYSYMH WNQQKPGQPPRLLIY LVSN

LESGVPARFSGSGSGTDFTLNIHPVEEEDAATYYC QHIRELTRSEGGPKWISN

CDR1: RASKSVSTSGYSYMH
CDR2: LVSN
CDR3: QHIRELTRSEGGPKWISN

SEQUENCE LISTING

<160> NUMBER OF SEQ ID NOS: 21

<210> SEQ ID NO 1
<211> LENGTH: 366
<212> TYPE: DNA
<213> ORGANISM: h. sapiens

<400> SEQUENCE: 1
gaggtgcagc tggtgcagtc tggcccagga ctggtgaagc cttcggagac cctgtccctc      60
acttgcactg tctctggtag ctccatgagg actcactatt ggacctggat ccggcagccc     120
ccagggaagg gactggagtg gattgggaac atctattaca gtgggagcac cgactacaac     180
ccctccctca gagtcgagt caccatatca gtagacacgt ccaagaacca gttctccctg     240
aaactgagct ctgtgaccgc cgcagacacg gccgtgtatt tttgtgcgag aacaaaacac     300
ttcgatattt tgcccggggg tgttttttgat atgtggggcc agggaccac ggtcaccgtc     360
tcctca                                                                 366

<210> SEQ ID NO 2
<211> LENGTH: 321
<212> TYPE: DNA
<213> ORGANISM: H. sapiens

<400> SEQUENCE: 2
tcttcctatg agctgacgca gctaccctca gtgtccgtgt ccccaggaca gacagccacc      60
atcacctgct ctggagatag attgggggat aaatatgctt gctggtatca gcagaagcca     120
ggccagtccc ctgtgctggt catctttcaa gataccaagc ggccctcagg gatccctgag     180
cgattctctg gctccaactc tgggaacaca gccactctga ccatcagcgg gacccaggct     240
atggatgagg ctgactatta ctgtcaggcg tgggacagca atattggggt attcggcgga     300
gggaccaagc tcaccgtcct a                                                321

<210> SEQ ID NO 3
<211> LENGTH: 375
<212> TYPE: DNA
<213> ORGANISM: H. sapiens

<400> SEQUENCE: 3
caggtgcagc tgcaggagtc gggcccagga ctggtgaaac cttcacagac cctgtccctc      60
acctgcgctg tctctggtgg ctccatcagc agtcgtggtt actactggag ttggatccgc     120
cagcccccag ggaagggcct ggagtggatt gggtacatct tttacacggg ggcaccgac      180
tacaacccgt ccctcaagag tcgaattacc atatcaagag acacgccaa gaaccagata     240
tccctgaatc tgagctctgt gactgccgca gacacggccg tgtattactg tgccagagtg     300
gtggatggta gtagtgggta tcatcattac tactttgact actggggcca gggaaccctg     360
gtcaccgtct cctca                                                       375

<210> SEQ ID NO 4
<211> LENGTH: 335
<212> TYPE: DNA
<213> ORGANISM: H. sapiens

<400> SEQUENCE: 4
tctgacatcc agatgaccca gtctcctgct tccttagctg tatctctggg gcagagggcc      60
accatctcat acagggccag caaaagtgtc agtacatctg gctatagtta tatgcactgg     120

```
aaccaacaga aaccaggaca gccacccaga ctcctcatct atcttgtatc caacctagaa    180
tctggggtcc ctgccaggtt cagtggcagt gggtctggga cagacttcac cctcaacatc    240
catcctgtgg aggaggagga tgctgcaacc tattactgtc agcacattag ggagcttaca    300
cgttcggagg ggggaccaag ctggagatca aacgt                               335

<210> SEQ ID NO 5
<211> LENGTH: 366
<212> TYPE: DNA
<213> ORGANISM: H. sapiens

<400> SEQUENCE: 5
caggtgcagc tgcaggagtc gggcccagga ctggtgaagc cttcggagac cctgtccctc     60
acttgcactg tctctggtag ctccatgagg actcactatt ggacctggat ccggcagccc    120
ccagggaagg gactggagtg gattgggaac atctattaca gtgggagcac cgactacaac    180
ccctccctca gagtcgagt caccatatca gtagacacgt ccaagaacca gttctccctg    240
aaactgagct ctgtgaccgc cgcagacacg gccgtgtatt tttgtgcgag aacaaaacac    300
ttcgatattt tgcccggggg tgtttttgat atgtggggcc agggacaat ggtcaccgtc    360 tcttca                                                              366

<210> SEQ ID NO 6
<211> LENGTH: 335
<212> TYPE: DNA
<213> ORGANISM: H. sapiens

<400> SEQUENCE: 6
tctgacatcg tgatgaccca gtctcctgct tccttagctg tatctctggg gcagagggcc     60
accatctcat acagggccag caaaagtgtc agtacatctg ctatagttta tatgcactgg    120
aaccaacaga aaccaggaca gccacccaga ctcctcatct atcttgtatc caacctagaa    180
tctggggtcc ctgccaggtt cagtggcagt gggtctggga cagacttcac cctcaacatc    240
catcctgtgg aggaggagga tgctgcaacc tattactgtc agcacattag ggagcttaca    300
cgttcggagg ggggaccaaa gtggatatca aacgt                               335

<210> SEQ ID NO 7
<211> LENGTH: 122
<212> TYPE: PRT
<213> ORGANISM: H. sapiens

<400> SEQUENCE: 7

Glu Val Gln Leu Val Gln Ser Gly Pro Gly Leu Val Lys Pro Ser Glu
  1               5                  10                  15

Thr Leu Ser Leu Thr Cys Thr Val Ser Gly Ser Ser Met Arg Thr His
             20                  25                  30

Tyr Trp Thr Trp Ile Arg Gln Pro Pro Gly Lys Gly Leu Glu Trp Ile
         35                  40                  45

Gly Asn Ile Tyr Tyr Ser Gly Ser Thr Asp Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Phe Cys Ala
                 85                  90                  95

Arg Thr Lys His Phe Asp Ile Leu Pro Gly Gly Val Phe Asp Met Trp
                100                 105                 110
```

```
Gly Arg Gly Thr Thr Val Thr Val Ser Ser
        115                 120
```

<210> SEQ ID NO 8
<211> LENGTH: 106
<212> TYPE: PRT
<213> ORGANISM: H. sapiens

<400> SEQUENCE: 8

```
Ser Tyr Glu Leu Thr Gln Leu Pro Ser Val Ser Val Ser Pro Gly Gln
  1               5                  10                  15

Thr Ala Thr Ile Thr Cys Ser Gly Asp Arg Leu Gly Asp Lys Tyr Ala
             20                  25                  30

Cys Trp Tyr Gln Gln Lys Pro Gly Gln Ser Pro Val Leu Val Ile Phe
         35                  40                  45

Gln Asp Thr Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Asn Ile Gly Val
                 85                  90                  95

Phe Gly Gly Gly Thr Lys Leu Thr Val Leu
            100                 105
```

<210> SEQ ID NO 9
<211> LENGTH: 125
<212> TYPE: PRT
<213> ORGANISM: H. sapiens

<400> SEQUENCE: 9

```
Gln Val Gln Leu Gln Glu Ser Gly Pro Gly Leu Val Lys Pro Ser Gln
  1               5                  10                  15

Thr Leu Ser Leu Thr Cys Ala Val Ser Gly Ser Ile Ser Ser Arg
             20                  25                  30

Gly Tyr Tyr Trp Ser Trp Ile Arg Gln Pro Pro Gly Lys Gly Leu Glu
         35                  40                  45

Trp Ile Gly Tyr Ile Phe Tyr Thr Gly Gly Thr Asp Tyr Asn Pro Ser
     50                  55                  60

Leu Lys Ser Arg Ile Thr Ile Ser Arg Asp Thr Pro Lys Asn Gln Ile
 65                  70                  75                  80

Ser Leu Asn Leu Ser Ser Val Thr Ala Ala Asp Thr Ala Val Tyr Tyr
                 85                  90                  95

Cys Ala Arg Val Val Asp Gly Ser Ser Gly Tyr His His Tyr Tyr Phe
            100                 105                 110

Asp Tyr Trp Gly Gln Gly Thr Leu Val Thr Val Ser Ser
        115                 120                 125
```

<210> SEQ ID NO 10
<211> LENGTH: 110
<212> TYPE: PRT
<213> ORGANISM: H. sapiens

<400> SEQUENCE: 10

```
Asp Ile Gln Met Thr Gln Ser Pro Ala Ser Leu Ala Val Ser Leu Gly
  1               5                  10                  15

Gln Arg Ala Thr Ile Ser Tyr Arg Ala Ser Lys Ser Val Ser Thr Ser
             20                  25                  30
```

```
Gly Tyr Ser Tyr Met His Trp Asn Gln Gln Lys Pro Gly Gln Pro Pro
            35                  40                  45

Arg Leu Leu Ile Tyr Leu Val Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Arg Ser Asn
            100                 105                 110
```

<210> SEQ ID NO 11
<211> LENGTH: 120
<212> TYPE: PRT
<213> ORGANISM: H. sapiens

<400> SEQUENCE: 11

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Ser Ser Met Arg Thr His
             20                  25                  30

Tyr Trp Thr Trp Ile Arg Gln Pro Pro Gly Lys Gly Leu Glu Trp Ile
            35                  40                  45

Gly Asn Ile Tyr Tyr Ser Gly Ser Thr Asp Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Phe Cys Ala
                85                  90                  95

Arg Thr Lys His Phe Asp Ile Leu Pro Gly Gly Val Phe Asp Met Trp
            100                 105                 110

Gly Arg Gly Thr Thr Val Ser Ser
            115                 120
```

<210> SEQ ID NO 12
<211> LENGTH: 110
<212> TYPE: PRT
<213> ORGANISM: H. sapiens

<400> SEQUENCE: 12

```
Asp Ile Val Met Thr Gln Ser Pro Ala Ser Leu Ala Val Ser Leu Gly
  1               5                  10                  15

Gln Arg Ala Thr Ile Ser Tyr Arg Ala Ser Lys Ser Val Ser Thr Ser
             20                  25                  30

Gly Tyr Ser Tyr Met His Trp Asn Gln Gln Lys Pro Gly Gln Pro Pro
            35                  40                  45

Arg Leu Leu Ile Tyr Leu Val Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Lys Trp Ile Ser Asn
            100                 105                 110
```

<210> SEQ ID NO 13
<211> LENGTH: 8

```
<212> TYPE: PRT
<213> ORGANISM: H. sapiens

<400> SEQUENCE: 13

Gly Ser Ser Met Arg Thr His Tyr
 1               5

<210> SEQ ID NO 14
<211> LENGTH: 7
<212> TYPE: PRT
<213> ORGANISM: H. sapiens

<400> SEQUENCE: 14

Ile Tyr Tyr Ser Gly Ser Thr
 1               5

<210> SEQ ID NO 15
<211> LENGTH: 16
<212> TYPE: PRT
<213> ORGANISM: H. sapiens

<400> SEQUENCE: 15

Ala Arg Thr Lys His Phe Asp Ile Leu Pro Gly Gly Val Phe Asp Met
 1               5                  10                  15

<210> SEQ ID NO 16
<211> LENGTH: 6
<212> TYPE: PRT
<213> ORGANISM: H. sapiens

<400> SEQUENCE: 16

Arg Leu Gly Asp Lys Tyr
 1               5

<210> SEQ ID NO 17
<211> LENGTH: 3
<212> TYPE: PRT
<213> ORGANISM: H. sapiens

<400> SEQUENCE: 17

Gln Asp Thr
 1

<210> SEQ ID NO 18
<211> LENGTH: 9
<212> TYPE: PRT
<213> ORGANISM: H. sapiens

<400> SEQUENCE: 18

Gln Ala Trp Asp Ser Asn Ile Gly Val
 1               5

<210> SEQ ID NO 19
<211> LENGTH: 9
<212> TYPE: PRT
<213> ORGANISM: H. sapiens

<400> SEQUENCE: 19

Lys Ser Val Ser Thr Ser Gly Ser Tyr
 1               5

<210> SEQ ID NO 20
<211> LENGTH: 3
<212> TYPE: PRT
<213> ORGANISM: H. sapiens
```

```
<400> SEQUENCE: 20

Leu Val Ser
 1

<210> SEQ ID NO 21
<211> LENGTH: 8
<212> TYPE: PRT
<213> ORGANISM: H. sapiens

<400> SEQUENCE: 21

Gln His Ile Arg Glu Leu Thr Arg
 1               5
```

US 7,879,326 B2

HUMAN NEUTRALIZING MONOCLONAL ANTIBODIES TO H5N1 INFLUENZA A VIRUS

FEDERALLY-SPONSORED RESEARCH OR DEVELOPMENT

This invention was made with Government support under contract AI070373 awarded by the National Institutes of Health. The Government has certain rights in this invention.

BACKGROUND OF THE INVENTION

Pandemic influenza is one of the largest infectious disease threats to the human population. These pandemics occur when novel influenza A viruses enter the human population having the potential to cause catastrophic disease. This potential is highlighted by the 1918 Spanish influenza pandemic that swept the globe on its way to infecting 25-40% of the world's population and killing millions of people. Influenza pandemics again emerged in 1957 and in 1968, each killing an estimated 1 million people during their first waves.

Influenza A virus subtype H5N1, also known as A(H5N1) or simply H5N1, is a subtype of the Influenza A virus which can cause illness in humans and many other animal species. A bird-adapted strain of H5N1, called HPAI A(H5N1) for "highly pathogenic avian influenza virus of type A of subtype H5N1", is the causative agent of H5N1 flu, commonly known as "avian influenza" or "bird flu". It is endemic in many bird populations, especially in Southeast Asia.

While there is not yet efficient human-to-human transmission or airborne transmission of H5N1 to humans, the virus does have a high mortality rate when humans are infected, and Influenza A is capable mutation and reassortment, which could lead to a more effectively transmitted disease. Certain events have taken place that could increase the possibility of a pandemic, including the spread of disease to new areas through migratory birds.

Another set of issues is that phylogenic and genetic analyses of the H5N1 viruses circulating in Asia have identified three main clades of contemporary virus, see Chen et al. (2005) Nature 436:191-192. The viruses isolated in Vietnam, Thailand, Malaysia, Cambodia, and Laos belong to one group (clade II), the viruses from Indonesia (and some from China) represent another (clade III), and the viruses from migratory birds in China (and probably Russia) make up the third (clade I). Genetic analysis has identified six subclades of clade 2, three of which have a distinct geographic distribution and have been implicated in human infections. Antigenically, the isolates from groups I and II are distinct. Unfortunately, antigenic information concerning the group III viruses is limited, but phylogeny of the HA gene suggests that it too will be distinct from viruses of the other groups. Because it cannot be predicted from which H5N1 group the pandemic virus may emerge, it is necessary that any vaccination or antiviral strategy have the capacity to inhibit viruses from each. A critical question of the current vaccines in clinical studies is their ability to induce cross-clade neutralizing antibodies. Antibodies against H5N1 are discussed by Simmons et al. (2007) PLOS 4:e178.

The extreme virulence of this virus and its growing geographic distribution urge the development of targeted therapeutic and prophylactic measures. Already H5N1 vaccines have entered clinical trials worldwide and they offer the best means of mass protection. However, it is likely the first line of defense against an emerging pandemic will need other options including antivirals. In addition, for certain patients such as the elderly, infants, and immunocompromised hosts, a limited response to vaccination will require other preventive measures.

Currently, the two options for treating influenza are the M2 ion channel blockers (e.g., amantadine) and the neuraminidase inhibitors (e.g., oseltamivir and zanamivir). Unfortunately, many of the current H5N1 viruses are resistant to amantadine and a higher dose and longer treatment schedule of oseltamivir is needed for protection in murine models, proof that other options are very much needed.

An alternative prevention measure is to develop antibody-based therapeutics to neutralize viruses representing each of the three clades, or cross-clades. Preventing disease with specific high-titer antibody preparations has been established for a wide-range of infectious agents including hepatitis A virus, hepatitis B virus, herpesviruses (VZV and CMV), rabies, and measles. The value of specific antibodies in treating infectious disease has been also demonstrated for transplant recipients with CMV infection (in combination with ganciclovir), parvovirus B19 in immunocompromised patients, and RSV infection in premature infants to name a few examples. These antibody preparations are mostly derived from human polyclonal sera although in recent years humanized monoclonal antibodies have been developed.

Due to the high lethality and virulence of H5N1, its endemic presence, its increasingly large host reservoir, and its significant ongoing mutations, the H5N1 virus presents a serious pandemic threat. Agents that can be used in the prevention or treatment of this disease are of great interest.

SUMMARY OF THE INVENTION

Compositions and methods are provided relating to human anti-H5N1 monoclonal antibodies. The antibodies of the invention bind to and neutralize H5N1 influenza virus across clades. Embodiments of the invention include isolated antibodies and derivatives and fragments thereof, pharmaceutical formulations comprising one or more of the human anti-H5N1 monoclonal antibodies; cell lines that produce these monoclonal antibodies. Also provided are CDR amino acid sequences, as shown in FIGS. 6-8, which may confer the cross-clade reactivity of these monoclonal antibodies. These sequences and the cognate epitopes to which the monoclonal antibodies of the invention bind can be used to identify other antibodies that specifically bind and neutralize H5N1; and immunotherapeutic methods for prevention of disease associated with H5N1 virus. Antibodies of interest include the provided BF1-1, BF1-10 and BF1-19, and variants thereof. The monoclonal antibodies of the invention find particular utility as reagents for the diagnosis and immunotherapy of disease associated with H5N1 virus in humans. An advantage of the monoclonal antibodies of the invention derives from the fact that they are encoded by a human polynucleotide sequence. Thus, in vivo use of the monoclonal antibodies of the invention for immunotherapy greatly reduces the problems of significant host immune response to the passively administered antibodies.

The human anti-H5N1 antibody may have a heavy chain variable region comprising the amino acid sequence of CDR1 and/or CDR2 and/or CDR3 of the provided human monoclonal human antibodies as shown in FIGS. 6-8; and/or a light chain variable region comprising the amino acid sequence of CDR1 and/or CDR2 and/or CDR3 of the provided human monoclonal human antibodies as shown in FIGS. 6-8. In other embodiments, the antibody comprises an amino acid sequence variant of one or more of the CDRs of the provided human antibodies, which variant comprises one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants). Such variants will normally having a binding affinity for human H5N1 of at least about $10^8$ KD, and will bind to the same epitope as an antibody having the amino acid sequence of those set forth in FIGS. 6-8.

In some embodiments of the invention, antibodies compete for binding with BF1-1, BF1-10 or BF1-19, e.g. compete for binding to H5N1 virus or polypeptides derived therefrom. Some antibodies are readily defined using the methods described herein.

Various forms of the antibodies are contemplated herein. For example, the anti-H5N1 antibody may be a full length antibody, e.g. having a human immunoglobulin constant region of any isotype, e.g. IgG1, IgG2a, IgG2b, IgG3, IgG4, IgA, etc. or an antibody fragment, e.g. a F(ab')$_2$ fragment, and F(ab) fragment, etc. Furthermore, the antibody may be labeled with a detectable label, immobilized on a solid phase and/or conjugated with a heterologous compound.

Diagnostic and therapeutic uses for the antibody are contemplated. In one diagnostic application, the invention provides a method for determining the presence of H5N1 virus comprising exposing a sample suspected of containing the H5N1 virus to the anti-H5N1 antibody and determining binding of the antibody to the sample. For this use, the invention provides a kit comprising the antibody and instructions for using the antibody to detect the H5N1 virus.

The antibodies of the invention are particularly efficacious in the prevention if disease before exposure or within a short period of time following exposure, usually less than about 5 days following exposure. Treatment may be systemic or localized, e.g. delivery by inhalation, nasal spray, etc., where a local delivery of particular interest is delivery to the respiratory system, e.g. to the lungs and/or nasal passages. For example, a lyophilized antibody preparation can be used for aerosol delivery to the lungs as a spray, in a nebulizer, as a dry powder, etc. In some embodiments, antibodies for localized delivery are mucosal antibodies, i.e. having an IgA constant region. In other embodiments the antibody has an IgG constant region, or is delivered as an Fab fragment.

The invention further provides: isolated nucleic acid encoding the antibodies and variants thereof as set forth in FIGS. 3-5; a vector comprising that nucleic acid, optionally operably linked to control sequences recognized by a host cell transformed with the vector; a host cell comprising that vector; a process for producing the antibody comprising culturing the host cell so that the nucleic acid is expressed and, optionally, recovering the antibody from the host cell culture (e.g. from the host cell culture medium). The invention also provides a composition comprising one or more of the human anti-H5N1 antibodies and a pharmaceutically acceptable carrier or diluent. This composition for therapeutic use is sterile and may be lyophilized, e.g. being provided as a pre-pack in a unit dose with diluent and delivery device, e.g. inhaler, syringe, etc.

BRIEF DESCRIPTION OF THE DRAWINGS

FIGS. 3A-3B provide the nucleotide sequence of the variable regions of the heavy and light chains of BF1-1 antibody, SEQ ID NO:1 and SEQ ID NO:2, respectively.

FIG. 4A-4B provide the nucleotide sequence of the variable regions of the heavy and light chains of BF1-10 antibody, SEQ ID NO:3 and SEQ ID NO:4, respectively.

FIG. 5A-5B provide the nucleotide sequence of the variable regions of the heavy and light chains of BF1-19 antibody, SEQ ID NO:5 and SEQ ID NO:6, respectively.

FIG. 6A-6B provide the amino acid sequence of the variable regions of the heavy and light chains of BF1-1 antibody, and showing the CDR 1, 2 and 3 regions, as underlined, SEQ ID NO:7 and SEQ ID NO:8, respectively.

FIG. 7A-7B provide the amino acid sequence of the variable regions of the heavy and light chains of BF1-10 antibody, and showing the CDR 1, 2 and 3 regions, as underlined, SEQ ID NO:9 and SEQ ID NO:10, respectively.

FIG. 8A-8B provide the amino acid sequence of the variable regions of the heavy and light chains of BF1-19 antibody, and showing the CDR 1, 2 and 3 regions, as underlined, SEQ ID NO:11 and SEQ ID NO:12, respectively.

DETAILED DESCRIPTION OF THE INVENTION

Figure 1:
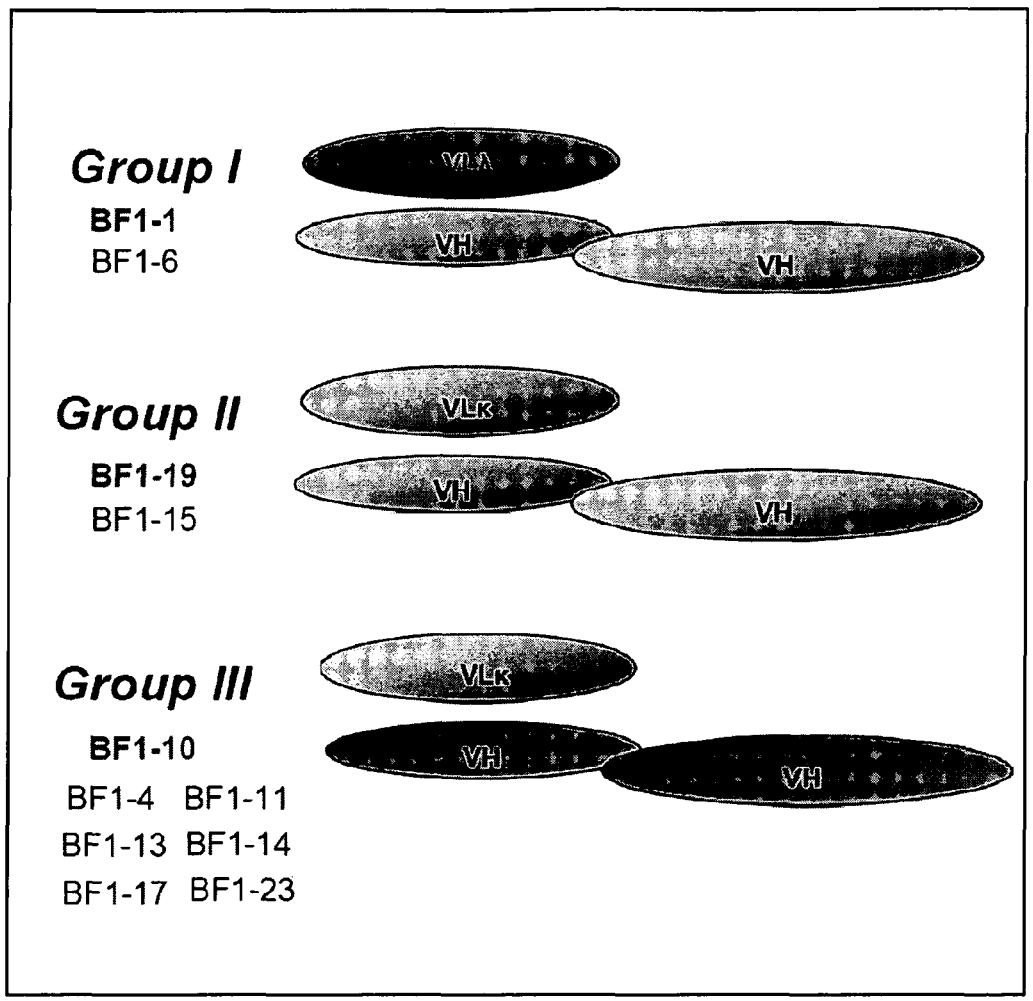
FIG. 1 is a schematic of the groups of monoclonal antibodies of the invention.

The present invention relates to human monoclonal antibodies which are specific for, and neutralize influenza virus (H5N1). In a preferred embodiment of the invention, human monoclonal antibodies are disclosed which are capable of binding epitopic polypeptide sequences in H5N1, and that bind to H5N1 viruses across at least two clades. Also disclosed is a nucleic acid, and amino acid sequence of such antibodies. The antibodies find use in immunotherapeutic methods for prevention of disease associated with H5N1 virus.

The term "H5N1" when used herein refers to an influenza A virus. The H5N1 may be isolated from a natural source of the virus, or viral polypeptides may be produced by synthetic means, e.g. using recombinant DNA technology. Exemplary amino acid sequences of H5N1 is described in Chen et al. Genomic signatures of human versus avian influenza A viruses. Emerg Infect Dis. 2006 Sep. Such sequences are publicly available, e.g. from the Centers for Disease Control.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

The term "H5N1 associated disease" means any disease caused, directly or indirectly, by H5N1 influenza virus. Influenza is a viral respiratory infection causing fever, coryza, cough, headache, and malaise. Mortality is possible during epidemics, particularly among high-risk patients, e.g. those who are institutionalized, at the extremes of age, have cardiopulmonary insufficiency, or are in late pregnancy. Diagnosis is usually clinical and depends on local epidemiologic patterns.

Influenza produces widespread sporadic illness yearly during fall and winter in temperate climates. Epidemics in the US occur about every 2 to 3 yr, most often caused by influenza A viruses. Pandemics caused by new influenza A serotypes may cause particularly severe disease. Influenza B viruses typically produce mild disease but can cause epidemics with moderate or severe disease, usually occurring in 3- to 5-yr cycles. Although most influenza epidemics result from a single serotype, different influenza viruses may appear sequentially in one location or may appear simultaneously, with one virus predominating in one location and another virus predominating elsewhere.

Influenza viruses may be spread by airborne droplets, person-to-person contact, or contact with contaminated items. Airborne spread appears to be the most important mechanism.

Patients with underlying cardiopulmonary disease, metabolic disease (especially diabetes mellitus) that requires regular medical attention, renal insufficiency, hemoglobinopathies, or immunodeficiency are at increased risk for severe disease. Women in the 2nd or 3rd trimester of pregnancy, children <24 mo, and adults >65 yr are also at increased risk. Morbidity and mortality in these patients may be due to exacerbation of underlying illness, primary influenza pneumonia, or secondary bacterial pneumonia.

The incubation period ranges from 1 to 4 days with an average of about 48 h. In mild cases, many symptoms are like those of a common cold (eg, sore throat, rhinorrhea); mild conjunctivitis may also occur. Typical influenza in adults is characterized by the sudden onset of chills, fever, prostration, cough, and generalized aches and pains (especially in the back and legs). Headache is prominent, often with photophobia and retrobulbar aching. Respiratory symptoms may be mild at first, with scratchy sore throat, substernal burning, nonproductive cough, and sometimes coryza. Later, lower respiratory tract illness becomes dominant; cough can be persistent, raspy, and productive. Children may have prominent nausea, vomiting, or abdominal pain, and infants may present with a sepsis-like syndrome. After 2 to 3 days, acute symptoms rapidly subside, although fever may last up to 5 days. Cough, weakness, sweating, and fatigue may persist for several days or occasionally for weeks.

Pneumonia is suggested by a worsening cough, purulent or bloody sputum, dyspnea, and rales. Secondary bacterial pneumonia is suggested by persistence or recurrence of fever, cough, and other respiratory symptoms in the 2nd wk.

Encephalitis, myocarditis, and myoglobinuria develop infrequently, usually during convalescence. The cause is unclear, but they occur more frequently after influenza A pandemics.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, $IgA_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, $F(ab')_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made in an immortalized B cell or hybridoma thereof, or may be made by recombinant DNA methods.

The monoclonal antibodies herein include hybrid and recombinant antibodies produced by splicing a variable (including hypervariable) domain of an anti-H5N1 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, $F(ab')_2$, and Fv), so long as they exhibit the desired biological activity.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 75% by weight of antibody as determined by the Lowry method, and most preferably more than 80%, 90% or 99% by weight, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "epitope tagged" when used herein refers to an anti-H5N1 antibody fused to an "epitope tag". The epitope tag polypeptide has enough residues to provide an epitope against which an antibody can be made, yet is short enough such that it does not interfere with activity of the H5N1 antibody. The epitope tag preferably is sufficiently unique so that the antibody specific for the epitope does not substantially cross-react with other epitopes. Suitable tag polypeptides generally have at least 6 amino acid residues and usually between about 8-50 amino acid residues (preferably between about 9-30 residues). Examples include the c-myc tag and the 8F9, 3C7, 6E10, G4, B7 and 9E10 antibodies thereto (Evan et al., Mol. Cell. Biol. 5(12):3610-3616 (1985)); and the Herpes Simplex virus glycoprotein D (gD) tag and its antibody (Paborsky et al., Protein Engineering 3(6):547-553 (1990)).

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

Polypeptides

In one aspect, the present invention is directed to combinatorially derived human monoclonal antibodies which are specifically reactive with and neutralize H5N1, and cell lines which produce such antibodies. Variable regions of exemplary antibodies are provided, e.g. SEQ ID NO:7 and 8; SEQ ID NO:9 and 10, SEQ ID NO:11 and 12. Antibodies of interest include these provided combinations, as well as fusions of the variable regions to appropriate constant regions or fragments of constant regions, e.g. to generate F(ab)' antibodies. Variable regions of interest include at least one CDR sequence, for example as shown in FIGS. 6-8, where a CDR may be 3, 4, 5, 6, 7, 8, 9, 10, 11, 12 or more amino acids, as shown in the Figures. Alternatively, antibodies of interest include a variable region as set forth in SEQ ID NO:7-12, or pairs of variable regions sequences as set forth in SEQ ID NO:7-8, 9-10, and 11-12.

In some embodiments a polypeptide of interest has a contiguous sequence of at least about 10 amino acids as set forth in any one of SEQ ID NO:7-12, at least about 15 amino acids, at least about 20 amino acids, at least about 25 amino acids, at least about 30 amino acids, up to the complete provided variable region. Polypeptides of interest also include variable regions sequences that differ by up to one, up to two, up to 3, up to 4, up to 5, up to 6 or more amino acids as compared to the amino acids sequence set forth in any one of SEQ ID NO:7-12. In other embodiments a polypeptide of interest is at least about 80%, at least about 85%, at least about 90%, at least about 95%, at least about 99% identical to the amino acid sequence set forth in any one of SEQ ID NO:7-12.

The isolation of cell lines producing monoclonal antibodies of the invention can be accomplished using routine screening techniques which permit determination of the elementary reaction pattern of the monoclonal antibody of interest. Thus, if a human monoclonal antibody being tested binds to the cognate epitope of one of the provided antibodies, i.e. cross-blocks, and neutralizes H5N1, then the human monoclonal antibody being tested and the human monoclonal antibody produced by the cell lines of the invention are equivalent.

It is also possible to determine, without undue experimentation, if a human monoclonal antibody has the same specificity as a human monoclonal antibody of the invention by ascertaining whether the former prevents the latter from binding to H5N1. If the human monoclonal antibody being tested competes with the human monoclonal antibody of the invention, as shown by a decrease in binding by the human monoclonal antibody of the invention, then the two monoclonal antibodies bind to the same, or a closely related, epitope. Still another way to determine whether a human monoclonal antibody has the specificity of a human monoclonal antibody of the invention is to pre-incubate the human monoclonal antibody of the invention with H5N1 with which it is normally reactive, and then add the human monoclonal antibody being tested to determine if the human monoclonal antibody being tested is inhibited in its ability to bind H5N1. If the human monoclonal antibody being tested is inhibited then, in all likelihood, it has the same, or functionally equivalent, epitopic specificity as the monoclonal antibody of the invention. Screening of human monoclonal antibodies of the invention can be also carried out utilizing H5N1 and determining whether the monoclonal antibody neutralizes H5N1.

In addition to Fabs, smaller antibody fragments and epitope-binding peptides having binding specificity for at least one epitope of H5N1 are also contemplated by the present invention and can also be used to neutralize the virus. For example, single chain antibodies can be constructed according to the method of U.S. Pat. No. 4,946,778 to Ladner et al, which is incorporated herein by reference in its entirety. Single chain antibodies comprise the variable regions of the light and heavy chains joined by a flexible linker moiety. Yet smaller is the antibody fragment known as the single domain antibody, which comprises an isolate VH single domain. Techniques for obtaining a single domain antibody with at least some of the binding specificity of the intact antibody from which they are derived are known in the art. For instance, Ward, et al. in "Binding Activities of a Repertoire of Single Immunoglobulin Variable Domains Secreted from *Escheria coli*," Nature 341: 644-646, disclose a method for screening to obtain an antibody heavy chain variable region (H single domain antibody) with sufficient affinity for its target epitope to bind thereto in isolate form.

Methods of Use

The human monoclonal antibodies of the invention can be used in vitro and in vivo to monitor the course of H5N1 disease therapy. Thus, for example, by measuring the increase or decrease in the number of cells infected with H5N1 or changes in the concentration of H5N1 present in the body or in various body fluids, it would be possible to determine whether a particular therapeutic regimen aimed at ameliorating the H5N1 disease is effective.

The monoclonal antibodies of the invention may be used in vitro in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of H5N1. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bio-luminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

For purposes of the invention, H5N1 may be detected by the monoclonal antibodies of the invention when present in biological fluids and tissues. Any sample containing a detectable amount of H5N1 can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Polynucleotides

The invention also provides isolated nucleic acids encoding the human anti-H5N1 antibodies, vectors and host cells comprising the nucleic acid, and recombinant techniques for the production of the antibody. Exemplary variable region sequences are provided in FIGS. 3-5, SEQ ID NO:1-6. Nucleic acids of interest may be at least about 80% identical to the provided nucleic acid sequences, at least about 85%, at least about 90%, at least about 95%, at least about 99%, or identical. In some embodiments a contiguous nucleotide sequence as set forth in any one of SEQ ID NO:1-6 of at least about 20 nt., at least about 25 nt, at least about 50 nt., at least about 75 nt, at least about 100 nt, and up to the complete provided sequence may be used. Such contiguous sequences may encode a CDR sequence, for example as shown in FIGS. 6-8, where a CDR may be 3, 4, 5, 6, 7, 8, 9, 10, 11, 12 or more amino acids, as shown in the Figures, or may encode a complete variable region. As is known in the art, a variable region sequence may be fused to any appropriate constant region sequence.

For recombinant production of the antibody, the nucleic acid encoding it is inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

The anti-H5N1 antibody of this invention may be produced recombinantly not only directly, but also as a fusion polypeptide with a heterologous or homologous polypeptide, which include a signal sequence or other polypeptide having a specific cleavage site at the N-terminus of the mature protein or polypeptide, an immunoglobulin constant region sequence, and the like. A heterologous signal sequence selected preferably may be one that is recognized and processed (i.e., cleaved by a signal peptidase) by the host cell. For prokaryotic host cells that do not recognize and process the native antibody signal sequence, the signal sequence is substituted by a prokaryotic signal sequence selected.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Suitable host cells for cloning or expressing the DNA are the prokaryote, yeast, or higher eukaryote cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2).

Host cells are transformed with the above-described expression or cloning vectors for anti-H5N1 antibody production and cultured in conventional nutrient media modified as appropriate for inducing promoters, selecting transformants, or amplifying the genes encoding the desired sequences.

In some embodiments of the invention, the provided human antibody variable regions and/or CDR regions are used in a screening method to select for antibodies optimized for affinity, specificity, and the like. In such screening methods, random or directed mutagenesis is utilized to generate changes in the amino acid structure of the variable region or regions, where such variable regions will initially comprise one or more of the provided CDR sequences, e.g. a framework variable region comprising CDR1, CDR2, CDR3 from the heavy and light chain sequences provided in FIGS. 6-8.

The mutated variable region sequences, which are optionally combined with a second variable region sequence, i.e. $V_H$VL, with constant regions, as a fusion protein to provide for display, etc., as known in the art. Methods for selection of antibodies with optimized specificity, affinity, etc., are known and practiced in the art, e.g. including methods described by Presta (2006) Adv Drug Deliv Rev. 58(5-6):640-56; Levin and Weiss (2006) Mol Biosyst. 2(1):49-57; Rothe et al. (2006) Expert Opin Biol Ther. 6(2):177-87; Ladner et al. (2001) Curr Opin Biotechnol. 12(4):406-10; Amstutz et al. (2001) Curr Opin Biotechnol. 12(4):400-5; Nakamura and Takeo (1998) J Chromatogr B Biomed Sci Appl. 715(1):125-36 each herein specifically incorporated by reference for teaching methods of mutagenesis selection. Such methods are exemplified by Wu et al. (2005) J. Mol. Biol. (2005) 350, 126-144.

Such screening methods may involve mutagenizing a variable region sequence comprising one or more CDR sequences set forth in any one of FIG. 6A, 6B, 7A, 7B, 8A or 8B; expressing the mutagenized sequence to provide a polypeptide product; contacting the polypeptide with an H5N1 antigen; identifying those polypeptide having the desired antigen affinity or specificity.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $CH_3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Formulations

Therapeutic formulations comprising one or more antibodies of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent the H5N1 associated disease.

The therapeutic dose may be at least about 0.01 μg/kg body weight, at least about 0.05 μg/kg body weight; at least about 0.1 μg/kg body weight, at least about 0.5 μg/kg body weight, at least about 1 μg/kg body weight, at least about 2.5 μg/kg body weight, at least about 5 μg/kg body weight, and not more than about 100 μg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like.

The antibody need not be, but is optionally formulated with one or more agents currently used to prevent or treat influenza. These are generally used in the same dosages and with administration routes as used hereinbefore or about from 1 to 99% of the heretofore employed dosages.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The formulation herein may also contain more than one active compound as necessary for the particular indication being treated, preferably those with complementary activities that do not adversely affect each other. For example, it may be desirable to further provide an antiviral agent, e.g. amantidine, tamiflu, etc. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

It is contemplated that the anti-H5N1 antibody of the present invention may be used to treat the various influenza associated diseases as described herein. In some embodiments, the recipient is at a high risk of infection, e.g. is immunocompromised, elderly, pediatric, etc., or is in a profession where the possibility of contact with infectious virus is high, e.g. medical staff, airline staff, military staff, and the like.

The anti-H5N1 antibody is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the anti-H5N1 antibody is suitably administered by pulse infusion, particularly with declining doses of the antibody.

For the prevention or treatment of disease, the appropriate dosage of antibody will depend on the type of disease to be treated, as defined above, the severity and course of the disease, whether the antibody is administered for preventive purposes, previous therapy, the patient's clinical history and response to the antibody, and the discretion of the attending physician. The antibody is suitably administered to the patient at one time or over a series of treatments.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-H5N1 antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention now being fully described, it will be apparent to one of ordinary skill in the art that various changes and modifications can be made without departing from the spirit or scope of the invention.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLE 1

Prevention with an effective H5N1 vaccine offers the best means for protection of the general population. However, the elderly, infants and immunocompromised patients with limited response to vaccination will require other preventive measures. Preventing disease with specific high-titer antibody preparations has been established for a wide-range of infectious agents.

Individuals were immunized with inactivated subvirion H5N1 as described by Treanor et al. (2006) N Engl J Med 354:1343-51, herein specifically incorporated by reference for teachings of vaccination strains and protocols.

A panel of IgG1 human monoclonal antibodies (HMAbs) to H5N1 were developed, where the panel contains three clusters of different antibodies, as represented by BF1-1, BF1-19 and BF1-10. BF1-1 and BF1-10 have distinct CDR 1, 2 and 3 regions of both heavy and light chains. Interestingly, BF1-19 has the same heavy chain as BF1-1 but the light chain of BF1-10.

Using a definition of ≧1:8 hemagglutination inhibition titer as positive inhibition, BF1-1 and BF1-19 neutralized viruses from Clade 1. BF1-10, having a different heavy chain CDR3, neutralized the same isolates from Clade 1 and Clade 2.3.

In vivo protection studies with a wild-type Clade 1 virus showed BF1-1 and BF1-19 at 1 mg/kg and 2.5 mg/kg given prior to infection provided respectively 80% and 100% protection. BF1-10 at 1 mg/kg and 2.5 mg/kg provided similar protection of 75-80%. Protection was also observed at 3 days but not 5 days post-infection.

These findings support the feasibility of isolating neutralizing HMAbs to epitopes conserved across clades, provide evidence that these cross-neutralizing antibodies can be elicited by H5N1 vaccination, and support a potential clinical utility to prevent and perhaps to treat recently exposed H5N1 infection.

Results

Selecting a B cell donor and isolating H5N1 HMAbs. Peripheral blood lymphocytes and corresponding sera were obtained from a group of individuals within 2-3 weeks of receiving their second dose of a prototype H5N1 vaccine (Treanor et al., supra.) Of 21 vaccinated donors, only three had serum antibody HI titers ≧160. These three individuals were previously vaccinated several years prior, to a prototype A/Hong Kong/156/97 vaccine. Compared to donors who only received the H5N1 vaccine, the sera from these three donors showed the broadest antibody profiles against a panel of H5N1 isolates.

The remaining individuals had titers of ≦20 to the immunizing subtype and no activity to other H5N1 isolates. These findings suggested long-lived immunological memory in the three A/Hong Kong/156/97 vaccinated individuals, a key element in a successful vaccine.

B cells from donor 34 were activated in microtiter plates using Epstein-Barr virus (EBV), screened for specific antibody secretion by either HI with inactivated virus or by IFA with Clade 1, H5N1 virus-infected MDCK cells. Cells from wells containing specific antibodies were used to generate human hybridomas as previously described (see Hadlock et al. (2000) *J. Virol.* 74:10407). Of over 80 monoclonal hybrids secreting H5N1 HMAbs, 12 were selected for further analyses based on their derivation from different pools of EBV-activated cells. Eleven HMAbs were HI-positive and one HI-negative.

Sequence analysis of the 11 HI-positive hybridoma Ig genes ($V_L$ and $V_H$) showed that these antibodies are in three clusters, as shown in FIG. 1 and derived from three independent B cells as represented by HMAbs designated as BF1-1, BF1-19 and BF1-10 (sequences provided as SEQ ID NO:1, 2 and 3). BF1-1 and BF1-10 have distinct CDR 1, 2 and 3 regions of both heavy and light chains.

Figure 2:
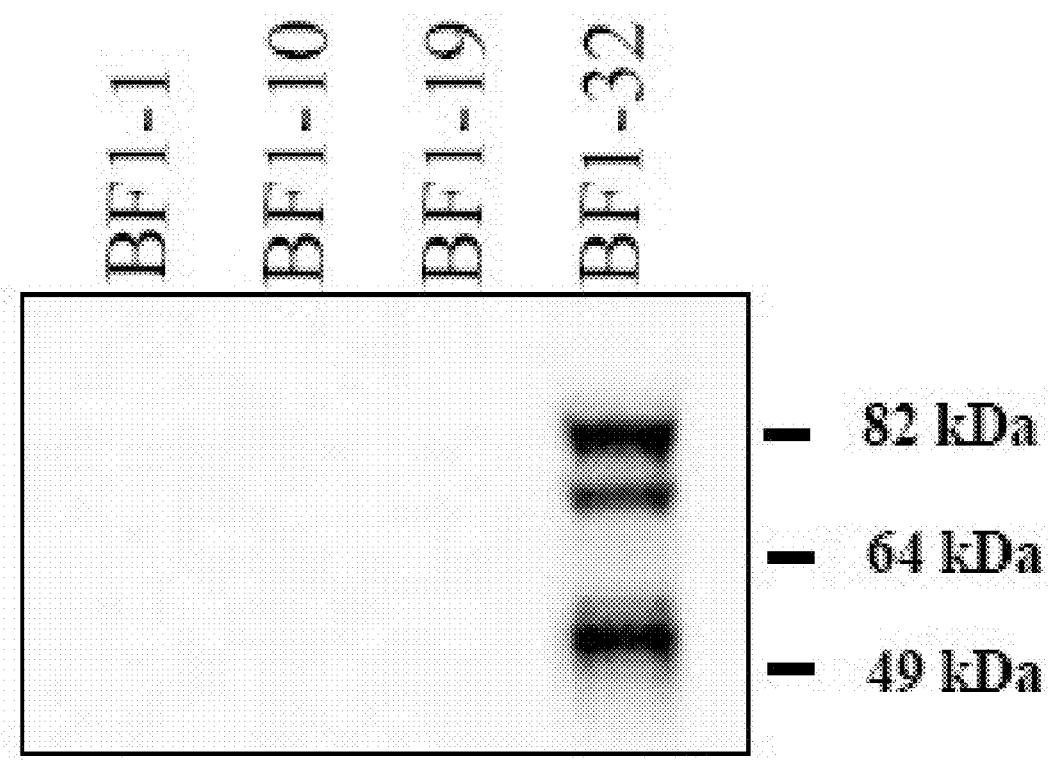
FIG. 2 is a western blot of the antibodies of the invention against a denatured H5N1 virus proteins.

Neutralizing H5N1 HMAbs are to conformational epitopes and of moderate affinity. Western Blot analysis of BF1-1, BF1-10, BF1-19 and BF1-32 were performed using Clade 1, H5N1 virus infected MDCK cell lysate is shown in FIG. 2A. All three HI-positive HMAbs, BF1-1, BF1-10 and BF1-19 showed no binding to denatured H5N1 antigens suggesting that these HMAbs are to conformational epitopes. The one HI-negative HMAb, BF1-32, is Western blot-positive and was identified by IFA with Clade 1, H5N1 virus infected MDCK cells. This antibody appears to target HA1 as the most prominent bands correspond to HA0, 82 Kd, and HA1, 58 Kd. Antibody binding affinity studies, KD, were performed by surface plasmon resonance (SPR) using a BIA-core 3000 instrument (Biacore, Uppsala, Sweden). In this system an anti-human IgG, Fcγ is covalently attached to the flow cells of a sensor chip and then used to capture each HMAb injected into the flow cells. Antibody association and disassociation kinetics can be determined using a range of purified H5N1 HA concentrations, as shown in FIG. 3 and Table 1. All three neutralizing HMAbs, BF1-1, BF1-10 and BF1-19 have a similar antibody binding affinity, $K_D$, between 10-50 nM.

TABLE 1

| Group | Antibody | KD (nM) |
|---|---|---|
| I | BF1-1 | 20.3 |
|  | BF1-6 | 30.4 |
| II | BF1-15 | 44.4 |
|  | BF1-19 | 48.2 |
| III | BF1-4 | 16.3 |
|  | BF1-10 | 10.8 |
|  | BF1-11 | 15.2 |
|  | BF1-13 |  |
|  | BF1-14 | 21.3 |
|  | BF1-17 |  |
|  | BF1-23 | 17.9 |

Using a definition of ≧1:8 titer as positive, testing was performed with spent supernatants from human hybridomas containing 10-40 µg/ml IgG. BF1-1 and BF1-19 neutralized A/HK/156/97 and Clade 1 H5N1 virus with identical patterns. The similarity is consistent with the observation that these two antibodies heavy chain CDR3 are the same, which is primarily responsible for antibody specificity. BF1-10 having a different heavy chain CDR3 neutralized the same two isolates plus Clade 2.3H5N1. The HI profiling observed with BF1-1 and BF1-19 demonstrated that these two HMAbs to a conserved epitope across two clades can be elicited in vaccinated individuals.

In vivo prevention and treatment studies in the mouse model. Prophylactic efficacy of neutralizing H5N1 HMAbs was tested in the H5N1 mouse model. BF1-1, BF1-10 and BF1-19 were each injected intraperitoneally into mice at the stated dose per kg prior to exposure to wild-type Clade 1 H5N1 virus. Of 6 mice in each group, BF1-1 and BF1-19 at 2.5 µg/kg provided complete protection. The level of protection with BF1-10 was slightly lower at 75%. The level of protection by BF1-1 and BF1-19 began to drop at 1 µg/kg.

To determine whether treatment with neutralizing H5N1 HMAbs leads to improved survival after infection, 2.5 µg/kg of each antibody was injected at day 1, 3 and 5 post-exposure. At 1 day post-exposure survival with all three HMAbs were at 100% and at 3 days post-exposure survival was at 80% for each antibody. A higher dosage survival at day 3 could improve survival. At day 5, with onset of symptoms, antibody treatment did not improve survival.

TABLE 3

Therapeutic efficacy of human monoclonals in H5N1 mouse model

| Treatment | PBS | BF1-1 | | | BF1-19 | | |
|---|---|---|---|---|---|---|---|
| Day of administration (relative to infection) | 1 | 1 | 3 | 5 | 1 | 3 | 5 |
| Percent survival | 0 | 100 | 80 | 0 | 100 | 80 | 0 |

What is claimed is:

1. An isolated human monoclonal antibody or variable region fragment thereof that specifically binds to H5N1, wherein:
the antibody heavy chain variable region comprises a CDR1 amino acid sequence (SEQ ID NO:13) GSSMR-THY; a CDR2 amino acid sequence (SEQ ID NO:14) IYYSGST and a CDR3 sequence (SEQ ID NO:15) ART-KHFDILPGGVFDM; and
the antibody light chain variable region comprises a CDR1 amino acid sequence (SEQ ID NO:16) RLGDKY, a CDR2 amino acid sequence (SEQ ID NO:17) QDT, a CDR3 amino acid sequence (SEQ ID NO:18) QAWD-SNIGV; or a light chain variable region comprising a CDR1 amino acid sequence (SEQ ID NO:19) KSVSTSGSY, a CDR2 amino acid sequence (SEQ ID NO:20) LVS, and a CDR3 amino acid sequence (SEQ ID NO:21) QHIRELTR.

2. An isolated human monoclonal antibody or variable region fragment thereof that specifically binds to H5N1, wherein the antibody comprises the variable region sequence of any one of BF1-1, BF1-10 or BF1-19.

3. An isolated polynucleotide encoding an antibody set forth in claim 1.

4. An isolated cell that produces an antibody set forth in claim 1.

5. A pharmaceutical composition comprising an antibody set forth in claim 1.

6. A pharmaceutical composition comprising set forth in claim 1, and a pharmaceutically acceptable excipient.

7. A method of preventing influenza infection, the method comprising the step of administering to a subject a therapeutically effective amount of an antibody set forth in claim 1 in a dose effective to prevent infection by an influenza virus.

8. The method of claim 7, wherein the influenza virus is H5N1.

9. The method of claim 8 further comprising step of administering a therapeutically effective amount of an anti-viral agent.

10. The method of claim 8, wherein the subject is human.

11. The method of claim 7, wherein the antibody is delivered locally to the respiratory system.

* * * * *